United States Patent [19]

Vaillancourt

[11] Patent Number: 4,743,243

[45] Date of Patent: May 10, 1988

[54] NEEDLE WITH VENT FILTER ASSEMBLY

[76] Inventor: Vincent L. Vaillancourt, 14 Bunyan Dr., Livingston, N.J. 07039

[21] Appl. No.: 779,935

[22] Filed: Sep. 25, 1985

Related U.S. Application Data

[63] Continuation-in-part of Ser. No. 567,877, Jan. 3, 1984, abandoned.

[51] Int. Cl.$^4$ ............................................ A61B 19/00

[52] U.S. Cl. ...................................... 604/405; 604/45; 604/126; 604/166; 604/411

[58] Field of Search ............................... 604/164-168, 604/900, 43-45, 126, 405, 411

[56] References Cited

U.S. PATENT DOCUMENTS

| | | | |
|---|---|---|---|
| 2,473,153 | 6/1949 | Lager | 604/405 |
| 2,541,272 | 2/1951 | Murphy | 604/44 |
| 3,157,481 | 11/1964 | Bujan | 604/405 |
| 4,096,860 | 6/1978 | McLaughlin | 604/44 |
| 4,294,594 | 10/1981 | Sloane, Jr. et al. | 604/126 |
| 4,298,358 | 11/1981 | Ruschke | 604/126 |
| 4,311,137 | 1/1982 | Gerald | 604/167 |
| 4,588,403 | 5/1986 | Weiss et al. | 604/414 |

OTHER PUBLICATIONS

Sterile Preparation for the Hospital Pharmacist Avis and Akers, © 1981.

*Primary Examiner*—C. Fred Rosenbaum
*Assistant Examiner*—Mark F. Colosimo

[57] ABSTRACT

This invention pertains to a molded vent needle housing which is adapted to retain a hydrophobic filter that removes unwanted impurities from the outside air and feeds air to and from the interior of a stoppered vial. This assembly includes a needle and a hub portion in flow communication therewith, this hub adapted for attachment to a syringe. The hydrophobic filter is secured in the molded housing and may be a disc or a cylindrical configuration. The housing has a bore in which the needle shank passes and a rigid sleeve member is secured to provide a small passageway for air flow. Several embodiments are shown, with some having a resilient seal and one having a shrink-wrap protector for both the exposed filter portions and providing a retaining member for an inserted O-ring. The outer sleeve member is removed so that the injecting needle and filled syringe are now ready for use.

4 Claims, 3 Drawing Sheets

NEEDLE WITH VENT FILTER ASSEMBLY

CROSS-REFERENCE TO RELATED APPLICATION

This is a continuing-in-part application of application Ser. No. 567,877 as filed in the U.S. Patent Office on Jan. 3, 1984. With the acceptance of this application and the transfer of the two sheets of drawings, the application Ser. No. 567,877 is expressly abandoned.

BACKGROUND OF THE INVENTION

1. Field of the Invention

The present invention relates to hypodermic needles used for injecting drugs into parenteral vials and removing the contents after mixing. Air venting of these vials is provided with this apparatus.

2. Description of the Prior Art

Heretofore, small volume parenteral fluid containers have been pierced with hypodermic needles connected to syringes to inject fluid for reconstitution. After reconstitution, the parenteral vial is repunctured and the contents removed. Alternately, a hypodermic needle-syringe combination is left within the vial while it is shaken and then the mixed drug is removed. Unfortunately, in this system the parenteral vial becomes pressurized during the procedure. As a result, a condition can and does occur which is known as "blowback" in which particles of drug are blown into the air. This "blowback" can be very harmful to the personnel preparing such drugs. These hazards are well documented. To overcome these hazards, it is recommended that the reconstituting vial be vented at all times. There are two common procedures used to accomplish this condition. In one procedure, a hypodermic needle is attached to a filter and is pierceably inserted into the parenteral vial. A second needle is attached to a syringe and is used to inject fluid into said vial. After securing the vented needle and syringe-needle combination, the contents are shaken and the reconstituted drug is aspirated into the syringe. The needle-syringe combination is withdrawn from the parenteral vial and is now ready for injection.

In the second procedure, an injection molded piercing pin is used. This piercing pin is approximately 0.2 inches (two tenths of an inch) in diameter and has two lumens or paths in this pin portion. One lumen is preattached to a syringe and the other lumen in the same pin to a vent to which a filter element is attached. U.S. Pat. No. 4,211,588 to RAINES shows such a device. This patent shows a method of making a molding of two pieces and with a spike portion in which separate passageways for air and fluid are provided. The size of the spike of this device prevents its use in some vial systems either because of the stopper size or the occurrence of leakage between the rubber stopper and the spike.

After piercing the parenteral vial with the piercing pin, fluid from the syringe is injected with air escaping through the vent lumen. The contents of the vial are shaken before withdrawal from the vial. After reconstitution (shaking), the drug is aspirated into the syringe through the other lumen. The piercing pin-syringe combination is now withdrawn from the parenteral vial. The fluid path is violated (broken) so as to remove the piercing pin assembly from the syringe and a hypodermic needle is now attached prior to injection.

Drawbacks are present in each of these two procedures. In the first procedure, two needle punctures are required; every time a vial is punctured, there is a risk of contamination. It is evident that the fewer times a container needs to be punctured, the more aseptic the interior. It is also to be noted that this procedure is a very clumsy one as the vial must be shaken while securing two needles and syringe which are attached thereto. This procedure requires much manipulation. In the second procedure, the hole area of the puncturing plastic pin is about twenty times that of a hypodermic needle. The removal of the plastic pin from the wet path and the application of a hypodermic needle to the nose of a wet syringe call for very strict protocols to avoid fluid-path contamination. The large bore resulting from the piercing of the rubber stopper by the molded piercing pin creates large quantities of rubber debris-particulates within the drug which are subsequently aspirated into the syringe and eventually find their way into the patient's circulatory system. The problem in reconstitution is that the mixed medicament be kept sterile during the use of needles and syringes. The syringe conventionally used by attendants is usually disposable and the wrapping insures initial sterility. A U.S. Pat. No. 3,822,909 to OGLE, as issued on May 13, 1975, shows air venting means and commercially produced auxiliary venting needles as in the first procedure are MILLEX-FG (TM of Millipore, Bedford, Mass.): The commercialization of the RAINES patent (U.S. Pat. No. 4,211,588) appears to be by Burron Medical Inc., Bethlehem, Pa., in their Chemo-Dispensing Pin TM. Accordingly, there is a need for a simpler, less cumbersome device which will overcome the problems aforementioned.

Venting apparatus is not new or apparatus that may be converted to include a vent is shown in other issued U.S. patents, among which is U.S. Pat. No. 2,541,272 to MURPHY, as issued Feb. 13, 1951. In this device, the sheath or sleeve, which is closed at its penetrating end, has an air passageway provided by a slot intermediate its extent. Another vent device using two channels is shown in U.S. Pat. No. 3,938,520, as issued to SCISLOWICZ et al, as issued Feb. 17, 1976, which shows a device which cannot be made small for a puncture or penetration of a resilient stopper. A dual flow catheter is shown in U.S. Pat. No. 4,096,860, as issued to McLAUGHLIN on June 27, 1978. This is a Y-block device and there is no suggestion or teaching of a filter in the Y-branch.

Also of note is U.S. Pat. No. 4,294,594, as issued to SLOANE, Jr. et al on Oct. 13, 1981. This is an in-line filter per se and does not pertain to a vented needle. U.S. Pat. No. 4,298,358, as issued to RUSCHKE on Nov. 3, 1981, shows a venting filter but there is no teaching of a combination with a needle. U.S. Pat. No. 4,311,137, issued to GERARD on Jan. 19, 1982, shows a Y-block device where air is filtered and fed to and from the needle channel through a branch portion. This is primarily an infusion device and does not show or teach venting of a mixing container.

SUMMARY OF THE INVENTION

This invention may be summarized, at least in part, with reference to its objects.

It is an object of this invention to provide, and it does provide, a needle assembly which provides initial penetration of a vial stopper in which an air venting means is provided by and with an outer sleeve needle which is in very close proximity to the injection needle carried by and on a syringe and provides an air vent and filter adapted to prevent unwanted "blowback" and developed pressures.

It is a further object of this invention to provide, and it does provide, a sleeve needle which may be adapted for penetration, and provides an air vent passageway and is connected to a hub portion that has an air vent and filter. This sleeve needle may be of plastic or metal and is attached to a hub portion of an injection needle by a silicone ring so that this outer sleeve and filter hub assembly may be slid from the injection needle and discarded just before the drug is injected into the patient. Alternately, this sleeve needle is removably connected to the filter assembly housing to which the injection needle is affixed. The sleeve needle is disconnected and slid from the injection needle and discarded just before the drug is injected into the patient.

This needle with vent filter is shown with variations, but essentially all assemblies provide a measure of protection of the injection needle as it is connected to a syringe. The vent of the passageway between the needle and sleeve provides vent means of the interior of the stoppered vial. This vent means includes a hydrophobic filter member that continuously provides communication of the vial with the atmosphere. In brief, the device embodying the teachings of this invention is capable of maintaining a continuous venting of the parenteral vial to the atmosphere. The piercing member (injection needle or sleeve needle depending upon the design) is a sharp cannula which presents a small cutting bore to the parenteral container's rubber or rubber-like closure, thereby minimizing particulates and avoiding leakage about the needle. Since the needle is preattached to the syringe, the fluid path is not broken. During reconstiution (shaking), only the needle and syringe assembly need to be held with the vial, thus minimizing the requirements for manual dexterity. The procedure of using this needle with a vent filter assembly is more direct, less subject to error and has fewer steps.

In one embodiment, the device includes a standard hypodermic (injection) needle with a female luer hub capable of being attached to a luer nose of a conventional syringe; a second sleeve needle is positioned below the injection needle and connected to a hub member with an air venting filter. A silicone rubber retaining ring hermetically seals the sleeve needle hub member to the hub of the injection (hypodermic) needle.

In a second embodiment, the device includes a standard hypodermic (injection) needle secured, using cement, insert molding, ultrasonic staking, etc., to the rear portion of the filter assembly having a female luer hub which is capable of being attached to a luer nose of a conventional syringe a second sleeve needle (which may be sharp) is sealed to a female luer hub using conventional sealing means and connected to the male luer hub of the forward portion of the air vent filter assembly. The annular space between the injection needle and sleeve needle allows air to enter and/or escape depending upon the condition of the parenteral vial. A hole near the entering end may be provided in the wall of the sleeve needle for air passage when the sleeve needle is used as a piercing member.

During puncture of said vial and reconstitution, the injection needle is substantially enclosed, virtually eliminating any probability or possibility of an operator's inadvertently touching the needle (touch contamination). It becomes unsheathed only after the drug is aspirated into the syringe and the needle with attached syringe assembly is withdrawn from the sleeve needle with vent filter assembly. The needle is now ready for injection into the patient.

Two embodiments are depicted with a disc-like filter arrangement. In one embodiment, the sleeve needle is attached to the female hub so that in an assembled condition the sleeve needle does not encase the sharpened end of the injection needle; and in another embodiment, the sleeve needle extends beyond the injecting needle. When the sleeve needle extends beyond the injecting needle, the sleeve needle is sharpened and may have a hole or slot (not shown) in the wall thereof to provide for air passage in the space between the sleeve needle and injecting needle when the outer sleeve needle is used as the piercing member.

Also shown are three embodiments wherein the vent filter housing is of tubular construction. In one arrangement, the sleeve needle is attached to a female luer hub of the housing and in alternate embodiments the sleeve needle is integrally molded with the vent filter housing or sealed thereto. In the first arrangement, the sleeve needle is removable from the vent filter housing which is affixed to the injection needle. In an alternate arrangement, an elastomeric washer is provided to seal the injection needle hub nose to the vent filter housing.

In fragmentary views there are shown two alternate retention constructions for the sleeve needle. In one the sleeve needle is of molded plastic and has means for a twist-off separation, and in the other the sleeve needle is a metal tube removably inserted in the vent filter housing.

In the several embodiments to be shown and described, it is to be noted that the injection needle is adapted to be attached to a syringe. The sleeve needle is a few thousandths of an inch larger in its interior diameter than the outer diameter of the injecting needle. The wall of this piercing needle is generally four-to ten-thousandths of an inch. Injection needle is preferably 20 gauge. This combination presents an outer bore that is much less than any known arrangement employing a two-lumen passageway. The outer sleeve needle is connected to the forward end of the filter assembly. This connection, which may be mechanical, weakened section, twist-off fitting or the like, provides means for not only maintaining the interior sterility of the injection needle, but also provides means for easy removal of the sleeve needle.

In an alternate embodiment, there is shown a needle with vent filter assembly in which the hub carrying the needle is inserted into a silicone O-ring that not only provides an exclusionary seal, but also promotes ready separation due to the nature of silicone rubber. This O-ring and the outer exposed surfaces of the filter are protected from accidental contact by the user. This protection is provided by a shrink plastic tube which, as later more fully described, not only secures this O-ring from accidental and unwanted dislodgement but protects the user from accidentally contacting the filter and thereby potentially causing damage such as blocking the filter, tearing or transporting hand oils, resulting in a change of filter properties. Each assembly contemplates using a hydrophobic membrane filter of 0.2 (two-tenths) micron in size.

The sleeve needle, unless used as the piercing needle, is smaller in length than the piercing needle. This sleeve needle may or may not be beveled at its distal end to provide easy penetration of a vial stopper.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of vented needle assemblies as adopted for use for reconstitution of a drug and showing preferred means for construction and using such apparatus for infeeding a medicament.

These specific embodiments have been chosen for the purposes of illustration and description as shown in the accompanying drawings wherein:

BRIEF DESCRIPTION OF THE DRAWINGS

FIG. 2 B represents a plan view, very fragmentary, and showing a vent hole formed in the side of the sleeve needle, this view taken on the line 2 B—2 B of FIG. 2 A and looking in the direction of the arrows;

FIGS. 6 A, 6 B, 6 C and 6 D represent progressive, diagrammatic side views, partly in section, of the vented needle and the reconstitution of drugs used therewith;

FIG. 12 A represents a sectional, transverse view taken on the line 12 A—12 A of FIG. 9 and looking in the direction of the arrows, and FIG. 12 B represents a transverse and rear view of the shrink wrap cover as positioned to retain an O-ring and as a protector cover for the filter areas that may be wetted by the contents of a vial or container during aspiration as in FIG. 6 D.

In the following description and in the claims, various details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

DETAILED DESCRIPTION OF FIG. 1

Figure 1:
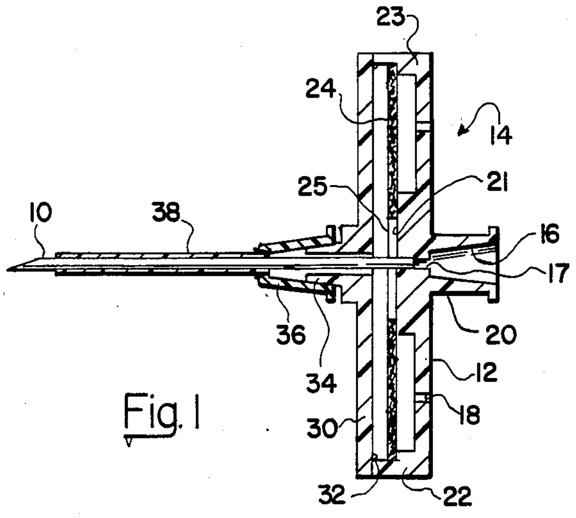
FIG. 1 represents a sectional side view of the device in an assembled condition, this view partly diagrammatic and showing a preferred construction of the needle with attached filter assembly.

Referring next to the drawings, and in particular to FIG. 1 there is depicted an assembly wherein the vent filter assembly is adapted to be removed from a luer nose of a syringe absent an injecting needle. The apparatus of FIG. 1 has a sharpened injecting cannula or needle 10 which is secured to and carried by a rear half 12 of a molded vent housing, generally identified as 14. In this rear half 12 is formed a luer female socket 16 terminating in a central passageway 17. One or more vent holes or passageways 18 is formed in said rear half. In this same half there is provided an interior hub portion 20 providing means to secure the injecting (piercing) needle. This hub has an interior face 21, and in an outer rim portion 22 of this rear half there is provided a stepped shoulder 23 which with surface 21 establishes a mounting plane.

A bacterial-excluding filter disk 24 is secured at its inner and outer diameters to the rear half 12. A clearance diameter portion 25 is formed when the disk 24 is cut, with this clearance 25 insuring that the injecting cannula 10 does not accidentally engage the filter disk 24. A front cover member 30 has a circular bead 32 to provide a locating and aligning means when sealing or welding of rear half 12 to front half 30 is achieved. This front half is molded to provide a male luer hub 34 on which is mounted a female luer hub 36 in which an outer sleeve needle 38 is secured.

The injecting needle 10 and the outer sleeve needle 38 are secured in the indicated hub portions by conventional methods such as cement, insert molding, ultrasonic staking and the like. The outer sleeve needle 38 is conventionally stainless steel and of thin-wall construction such as three- or four-thousandths of an inch in thickness. This sleeve needle may be, more or less, square-cut or may be formed with a sharpened bevel to assist in penetration of a parenteral vial stopper to be later identified.

It is to be noted that the outer sleeve needle 38 is attached at the small or left end of hub molding 36 and the interior of this hub is open to the passage of the injecting needle 10. The front half 30 is similarly formed to provide a free passageway for the shank of the injecting needle 10. The female luer hub 16 is conventional for attachment to a syringe. It is also to be noted that this vent filter assembly and housing 14 may be removed by mechanical means, weakened section or the like. It is essential that the sterility of the injection needle and the filter interior be maintained. The interior annular space between the outer diameter of the injection needle 10 and the inner diameter of the sleeve needle 38 is only a few thousandths of an inch. In this and the embodiments to be later identified and discussed, the filter is hydrophobic and of a 0.2 (two-tenths) micron in pore size.

DETAILED DESCRIPTION OF FIGS. 2 A AND 2 B

Figure 2B:
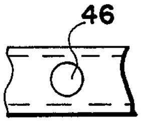
FIG. 2 A represents a sectional side view in an enlarged scale and showing the sleeve needle extending beyond the injecting needle, this view partly fragmentary to show only this alternate construction.
Figure 2A:
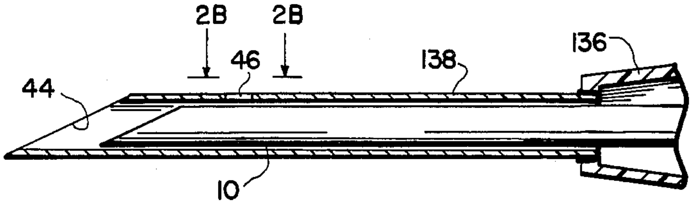

The drawings showing FIGS. 2 A and 2 B illustrate the arrangement of FIG. 1, but with a sleeve needle 138 extending beyond the injecting needle 10. This outer sleeve needle member 138 has a sharpened end 44, and to insure a free flow of air to and from the annular space between needles 10 and 138 there is formed a hole 46 in the side wall of member 138. This hole is to the rear of the sharpened end of the injecting needle 10. As shown, this sleeve needle member is secured to the front end of a molded luer hub 136, as noted above. In all other aspects, this embodiment performs as in FIG. 1 above.

IDETAILED DESCRIPTION OF FIG. 3

Figure 3:
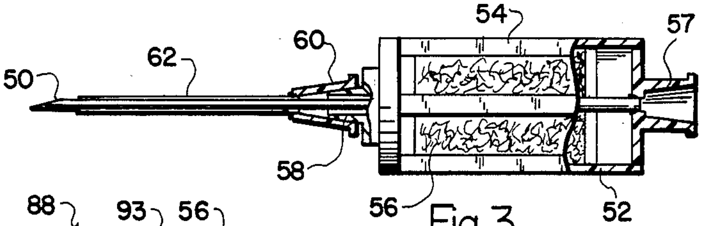
FIG. 3 represents a sectional side view in the scale of FIG. 1 and utilizing the same luer mounting arrangement, but with a tubular filter secured in and retained in a molded housing.

In FIG. 3 there is a showing of an assembly in which the mounting concept of FIG. 1 is shown, but rather than a disk filter there is shown a tubular filter much like that shown in the referenced application. In FIG. 3, injecting needle identified as 50 is longer than in the embodiment of FIG. 1. This injecting needle is sharpened on its entering end (left) and is secured to a housing 52 having a plurality of rib members 54 (four are illustrated) disposed to secure and retain a filter 56 in a tubular configuration. A female luer hub portion 57 is provided at the right end of this vent filter housing and is disposed for removable attachment to a syringe. The left end of the housing 52 is provided with a male luer hub 58. As seen in this FIG. 3, a female luer hub 60 engages and retains a sleeve needle 62 similar to or identical to that seen in FIG. 1 above.

DETAILED DESCRIPTION OF FIG. 4

Figure 4:
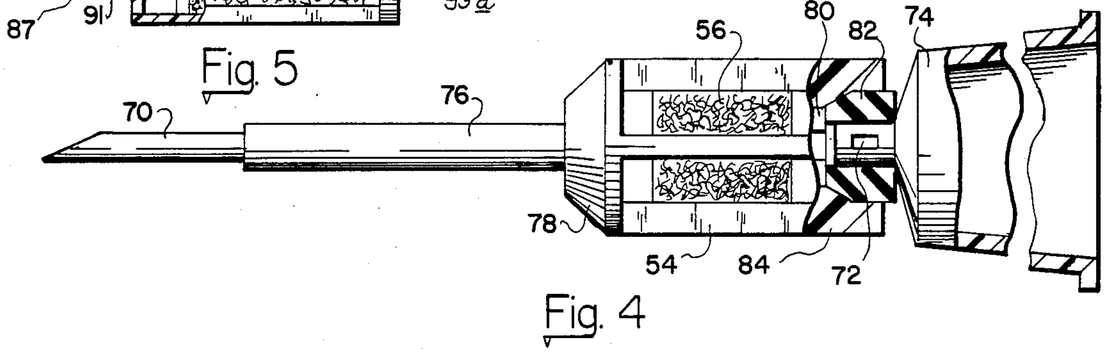
FIG. 4 represents in a slightly enlarged scale the sectional side view of a tubular filter assembly similar to that of FIG. 3, but with a silicone seal ring used to secure and retain the needle hub nose.

In FIG. 4 there is shown a sleeve-type filter very similar to that of FIG. 3, but showing a silicone rubber sleeve or ring to retain the filter housing to the nose of a hub and with the injecting needle secured to said extending nose of the hub. As depicted, injecting needle 70 is secured to an extending nose portion 72 of a hub 74. A sleeve cannula or needle 76 is secured to a molded tubular vent filter retainer housing 78. This housing molding has a plurality of rib members 54 retaining the filter 56 as in FIG. 3. The rear or right end of this housing 78 has a collar portion 80 in which a tapered recess 82 is formed. A silicone rubber ring seal 84 tightly engages the outer diameter of nose portion 72 of the hub 74. The outer diameter of this tapered seal 84 is a tight fit in the formed recess 82. This sleeve needle 76 is not sharpened and is to the rear of the sharpened end of the injecting needle 70.

DETAILED DESCRIPTION OF FIG. 5

Figure 5:
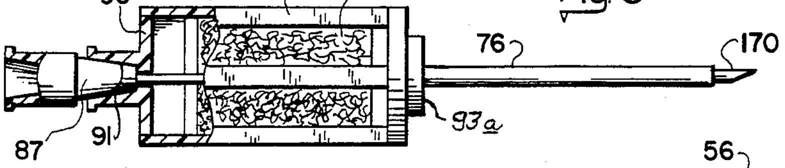
FIG. 5 represents a sectional side view of a tubular filter assembly similar to the apparatus of FIG. 4, but with the sleeve needle hub connected to the molded housing using a luer connector.

The embodiment of FIG. 5 is very like that shown in FIG. 4 above, but rather than using a silicone ring or sleeve the tubular filter is removably attached to a male luer hub. As depicted, an injection needle 170 is slideable in the outer sleeve needle 76. A filter membrane 56 is retained in a molded housing, generally indicated as 88. A male luer hub 87 is seated in a tapered socket 91 formed in hub end 90. This same hub 87 is shown as retaining, by cement, sonic welding, etc., the inner end of injection needle 170. Ribs 93 are formed when the molded housing is formed. The rear end of the sleeve needle 76 is fixedly secured in a boss end 93 a at the front end of the housing 88. It is to be noted that injection needle 170 may be retained on a male nose of a luer hub when and while the filter housing 88, the filter 56 and the sleeve needle 76 are discarded.

USE AND OPERATION OF THE APPARATUS AS SHOWN IN FIGS. 6 A, 6 B, 6 C AND 6 D

In the progression or steps of use depicted in FIGS. 6 A, B, C and D, the device of FIG. 1 is shown, but any of the vent assemblies of FIGS. 1 through 5 may be used with the same steps and results. A disposable conventional syringe 94 is depicted and a luer connection is usual, but other connections may be used.

In FIG. 6 A, it is assumed that a diluent vial 95 is closed with a resilient stopper 96 and contains therein a fluid diluent 97. A disposable syringe 94 is mounted in and on the housing assembly 14. An injecting needle 10 has its cutting end projecting beyond sleeve needle 38 and, as an assembly, the injection needle 10 and sleeve needle 38 are manipulated so as to pierce the stopper 96. The injection needle 10 is caused to enter the fluid 97 and syringe 94 is aspirated to withdraw said fluid from the vial 95 and into the syringe. The vent filter assembly 14 allows air 98 from the atmosphere to pass through filter 24 (FIG. 1) to and through the annular space between injection needle 10 and sleeve needle 38 into the vial during withdrawal of the fluid. This air flow pathway prevents a vacuum from being built up with the vial since air flows into the vial 95 as fluid is drawn into the syringe.

It is to be noted that exterior air is filtered through the membrane 24 and any and all bacteria exterior of the interior sterile environment are prevented from entering the stoppered vial 95 during withdrawal of the fluid 97. Air travels down the annular space between the injection needle 10 and sleeve needle 38, as noted above, and as a stream of bubbles 98 exits from the end of sleeve needle 38 and rises to the surface of the fluid diluent 97 within the vial 95. This flow of air provides equilibration of internal and external pressure. After filling the syringe 94, the now-filled syringe, the attached injection needle 10 and sleeve needle 38 are removed (withdrawn) from the stopper 96.

In FIG. 6 B is a depiction of a vial 99 having a stopper 100 which provides the desired hermetic seal closure of the interior contents. A parenteral drug 101 may or may not be a powder and may or may not be subject to vacuum. Vacuum is often used when extended life of the drug is desired. As depicted, the drug 101 is a powder or powdery substance.

In FIG. 6 C, the parenteral vial 99 of FIG. 6 B is shown with the stopper 100 pierced and penetrated with the injecting needle 10 and more particularly with the sleeve needle 38. The diluent 97 aspirated into the syringe 94 is caused to be injected into the vial from the end of injection needle 10 and within the sleeve needle 38. The piercing of the stopper 100 causes air to rush into the interior of the vial 99 when this vial is under vacuum. The vent and membrane allows the air pressure in vial 99 to be brought into equilibrium with external atmospheric pressure. The inflowing air is passed through the filter membrane 24 and down through the annular space between injection needle 10 and the outer sleeve needle 38. As diluent 97 is pushed into the vial 99 that excess air within the vial 99 is caused to flow (escape) through the annular space between injection needle 10 and sleeve needle 38 thence to vent. The distal end of the sleeve needle 38 is kept above the fluid level within the vial 99 during expelling of the fluid from the syringe 94.

After filling the vial 99 with fluid 97, said vial is shaken to assure mixing of the drug 101 and the diluent fluid) 97 to provide solution 102. When all of the drug 101 dissolved to provide said solution, the now mixed solution 102 is drawn into the syringe 94. As seen in FIG. 6 D the solution 102 is again aspirated into syringe 94. The injection needle assembly is pushed to and toward the stopper to a position near to the bottom of the vial 99 and as the syringe plunger is moved to fill the syringe with the mixed solution 102 air 98 flows down the annular pathway to maintain the atmospheric pressure within the vial 99. After the syringe 94 is filled to the desired capacity said injection needle assembly is withdrawn from the vial 99 by breaking the luer connection between the sleeve needle and vent filter housing. Alternately the entire assembly may be removed from the vial before breaking the aforementioned luer connection. The fitted injection needle syringe assembly is now used for injection. The injection needle 10 and syringe are now ready for use to dispense the medication.

APPARATUS OF FIG. 7

Figures 6A, 6B, 6C, 6D, 7, 8:
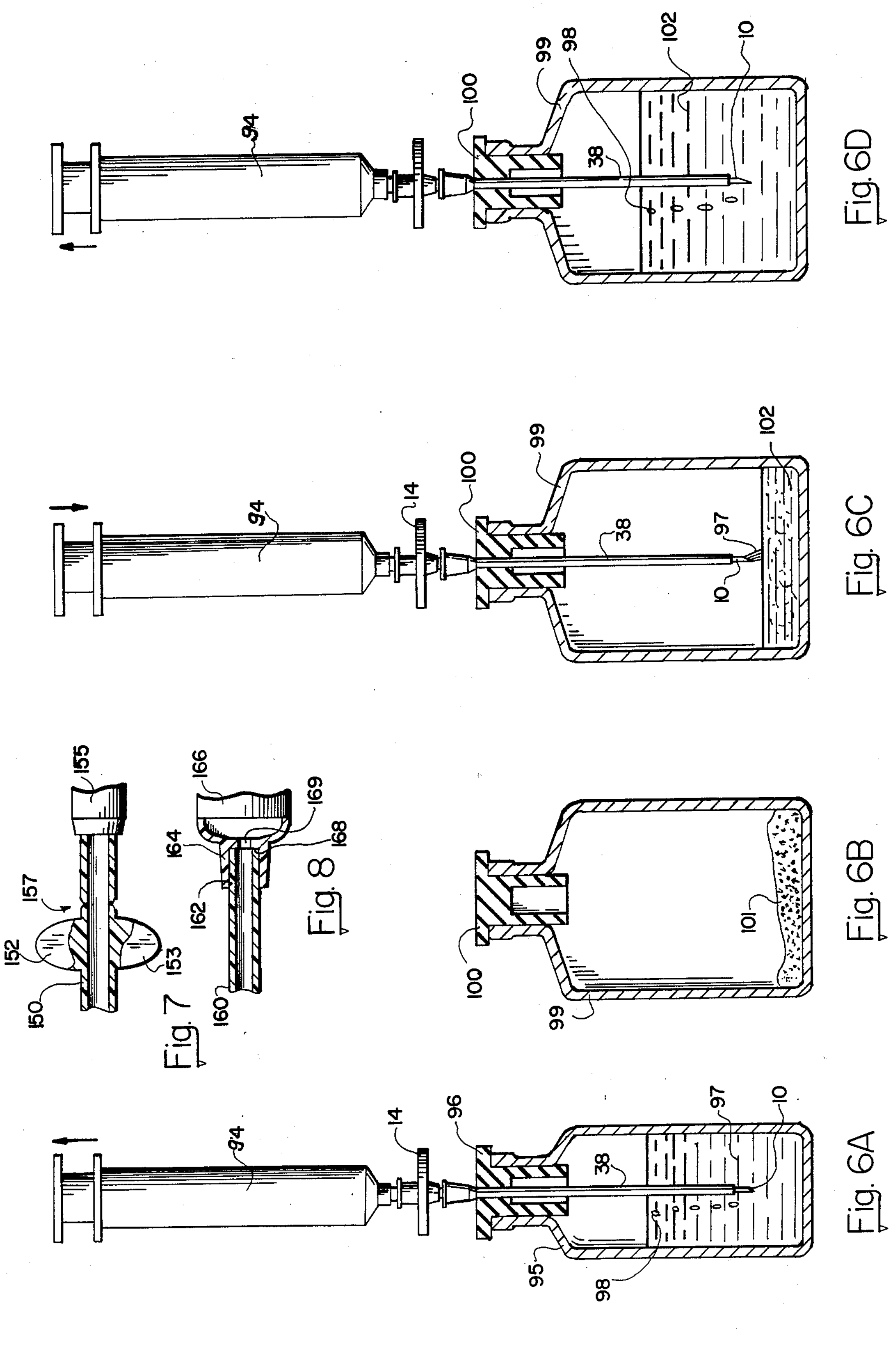
FIG. 7 represents a fragmentary and diagrammatic sectional side view and showing an outer sleeve cannula of plastic with ear extensions providing manipulating means for twisting off the sleeve member.
FIG. 8 represents a sectional side view, very fragmentary, and illustrating an outer sleeve needle removably mounted in a molded housing of the filter.

In FIG. 7 there is shown a very fragmentary sectional side view in which the sleeve needle is of plastic and has a weakened section encouraging the removal and discarding of said sleeve needle after filling syringe 94, as in FIG. 6 D, and prior to use of the injecting needle. As depicted, an outer sleeve portion 150 is of molded plastic and formed thereon is a plurality of ears 152 and 153. These ears as shown are two in number and are substantially diametrically opposite one another. Adjacent these ears and toward the molded housing 155 is a weakened area 157 which is in the nature of a ring or groove formed as the sleeve needle is molded. The housing 155 is illustrated as for a tubular filter membrane as shown in FIGS. 3, 4 and 5, but this concept may also be used with the disk housing of FIGS. 1 and 2. The molding of ears and a weakened area leading to a twist-off and discarding of the sleeve needle are proposed where and when the sleeve needle is of molded plastic and is provided with the filter housing.

APPARATUS OF FIG. 8

Referring next to FIG. 8, it is to be noted that a sleeve needle 160 is mountable in a recess 162 formed in a nose end 164 of a filter membrane housing 166. It is anticipated that the sleeve 160 will be an airtight fit in said recess and a shoulder or stop ring 168 limits the rearward or inward travel of this cannula in the recess. If desired, the sleeve needle may be made of metal. A clearance hole 169 provides a passageway for the injecting needle (not shown). This sleeve needle and its mounting technique lends itself to automatic and high-speed assembly.

USE AND OPERATION OF VENT FILTER OF FIGS. 1 THROUGH 8

In the several variations of the vent needle assembly as shown in FIGS. 1 through 8, it is contemplated that a syringe 94 be conventionally assembled for penetration of a stoppered vial. This penetration is shown diagrammatically in FIG. 6A. Whether the disc filter of FIG. 1 or the tubular filter of FIGS. 3, 4 and 5, it is contemplated that syringe 94 will be actuated to fill the syringe with liquid. This filled syringe with sleeve 38 is withdrawn and inserted into a mixing container 99 as in FIG. 6 C, with the needle and sleeve (penetrating) passing through the resilient stopper 100 after which this fluid 97 from the filled syringe is discharged into said container 99.

The vent needle assembly may be manipulated outwardly to move the sleeve and needle toward the stopper 100 to provide an escape conduit for any air at the top of the container 99 and displaced by an inflow of fluid from the syringe. After the fluid 97 is caused to be transferred into the container 99, the contents of the container are usually shaken to assure thorough mixing. The syringe is again aspirated (plunger drawn outwardly) to now draw the mixed medicant into the syringe 94. This may require repositioning the container 99 so that the medicant is caused to flow toward the stopper when and while the syringe and container are turned or nearly turned end-for-end. After filling the syringe with the desired amount of medicant, the needle and vent apparatus is withdrawn from the container 99. The vent sleeve 38 and associated components are now removed from the needle, exposing the needle 10 for injection of the medicant 102 from the syringe into a patient.

EMBODIMENT OF FIGS. 9, 10, 11, 12 A AND 12 B

Referring next, and finally, to the embodiment shown in FIGS. 9, 10, 11, 12 A and 12 B, there is depicted a vent filter needle assembly or device that lends itself to automatic and high-speed assembly production. A molded hub 200 has secured thereto a hollow needle 202, with this hub being notable as having a plurality of ribs 204 extending forwardly from a smooth diametrical surface 206 toward the needle shank and sharpened end 208. This hub is conventionally secured to the needle 202, with the hollow needle selected as to length and gauge diameter. Immediately to the right of this needle 202 is a tubular shrink-wrap member 210, to be more fully described later as to use. Still farther to the right is shown an O-ring 212 which is preferably made of silicone rubber having not only resilient properties but also release properties.

A molded retainer, generally identified as 216, has an internal recess 218 in which four rib-engaging, inwardly-extending, fin-like portions 220 are adapted to pass between and alongside the ribs 204 formed on the exterior of hub 200 as this hub is inserted into retainer 216. This recess 218, except for the fin-like portions 220, extends forwardly (to the right) to a front-end closure wall or member 222. It is to be noted that in forming the fin-like portions 220, there is provided a sloped stop shoulder, identified as 224, for a purpose to be explained below. In this end closure wall 222 are formed a tapered guideway and through bore or aperture 226 which extend through an integral cannula 228. The bore 226 in this cannula is greater in diameter than the outer diameter of the injection needle 202 passing there through. This differential in size from bore 226 to needle 202 provides a flow path for and of air and the like to and from a conventionally pierced vial as seen in FIG. 6 A. This clearance provides ready sliding movement of the needle 202 in and along the cannula 228.

The forward portion of housing 216 is formed with a plurality of external and outwardly-extending ribs or portions 230 which provide seating and gripping means for a needle shield 232 which is conventional and provides protection of and for the user so that the sharpened end 208 of the injection needle is not accidentally engaged. In the forward end of the molded member 216 is formed a plurality of V-grooves 234 which extend from the front or edge (right) to a hydrophobic filter 236 secured in a spaced relationship similar to the filters seen in FIGS. 3, 4 and 5.

ASSEMBLY AS IN FIGS. 9 AND 10

Figures 9, 10, 11, 12A, 12B:
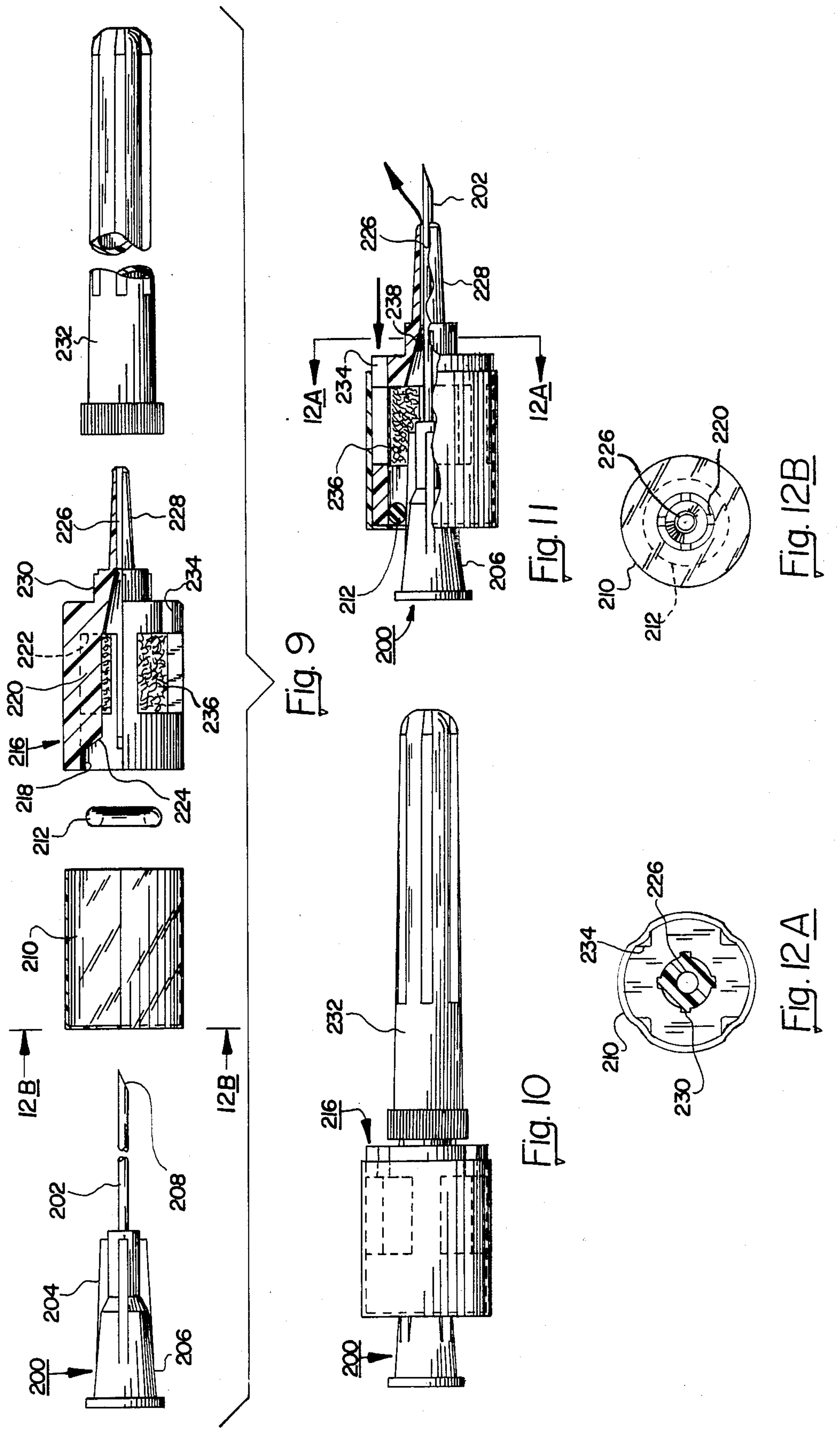
FIG. 9 represents an exploded side view, partly in section, of yet another embodiment of a needle with vent filter, this showing partly diagrammatic to illustrate the relationship of the several components.
FIG. 10 represents a side view of the needle with vent filter of FIG. 9 and showing an assembly of the several components in condition for shipment and prior to use.
FIG. 11 represents a side view, partly in section, and with arrows indicating the pathway of air transmittal to and from the needle end.

As depicted in FIG. 10, the molded retainer 216 of FIG. 9 has the cannula portion 228 and the filter portions 236 secured and formed during the molding operation. This filter may be a tubular portion inserted into the mold cavity before injection by a molten plastic or may include sonic or other cement securing. Whatever the process, it is assumed that molded retainer 216 is ready for the placement of the needle shield on the ribs 230. O-ring 212 is inserted into the cavity 218 and shrink sleeve 210 is placed over the housing and is shrunk into position as in FIG. 11. This shrink tubing is only a very few thousandths of an inch in thickness and preferably is clear or substantially translucent, but this is not of a critical importance. This sleeve when shrunk into position provides protection to all outwardly-facing filters so that accidental touching of these filter portions by the user is prevented. The shrink member 210 also extends a short distance at the left or open end of the retainer 216 so as to retain the O-ring 212 when inserted in the cavity 218 and to the sloped stop shoulder 224. This member 210 retains this O-ring against withdrawal movement of the injection needle 202.

DESCRIPTION OF FIG. 11

In FIG. 11 there is diagrammatically and partially sectionally shown the assembled device absent the needle shield 232 which is present prior to use. The vent needle assembly in FIG. 11 when attached to a syringe is ready for insertion into a stopper container 10 as in FIG. 6 A. The sharpened end 208 of injection needle 202 and the entering end of the rigid cannula 228 as seen in FIG. 11 are adapted to penetrate the stopper 96 (FIG. 6 A) and atmospheric air flows from the outside, as indicated by the arrow, and through V-groove 234 to and through the filter 236 into a tapered recess identified as 238, thence into the bore 226 in sleeve needle 228 and, as indicated by the arrow, into the container. The air flow passage may be reversed during filling as in FIG. 6 C. In this FIG. 11, the more-or-less diagrammatic showing has O-ring 212 seated on and engaging the shoulder 206 of the hub 200. Shrink-wrap member 210 extends downwardly and transversely across a portion of the cavity 218 shown and described in connection with FIG. 9 which is formed in the molded retainer 216. The rear portion of the shrink-wrap member 210 extends transversely or normal to the axis of the needle 202 sufficiently to provide a retaining rearward stop of and for O-ring 212 after assembly. This rear portion of the shrink-wrap member 210 does not extend to the hub portion 206.

EMBODIMENT OF FIG. 12 A

This view shows the formation of the V-grooves 234 (four shown) and indicates that the shrink-wrap 210 does not restrict air flow between the shrink-wrap and the V-grooves formed in the molding. Also seen are the ribs 230 which support and retain the needle shield 232 seen in FIGS. 9 and 10.

EMBODIMENT OF FIG. 12 B

FIG. 12 B is a view taken on the line 12 B—12 B of FIG. 9 and provides a diagrammatic showing of the relationship of the shrink-wrap member 210 on the member 216 and the O-ring 212 as seen in phantom outline. Also depicted are the bore 226 and the ribs 220 of the retainer 216.

USE AND OPERATION OF THE VENT FILTER OF FIGS. 9 THROUGH 12 B

This embodiment is particularly adapted to automatic assembly of a needle with vent filter device. It is contemplated that the injection needle 202 and attached hub 200 will be a commercially-produced and -available product. The needle shield 232, molded of rigid plastic, is also commercially produced and available. The retainer member 216 is a plastic molding and the filter portion or portions 236 are securely retained by or during the molding process. The securing of the filter is a selective procedure and is determined by the producer of the product. The resilient O-ring 212 is preferably of silicone rubber and is mounted in the recess 218 where it is a friction fit so as to retain this ring for further operations.

The thin plastic shrink-wrap sleeve 210, manufactured from PVC plastic, is cup-shaped and is heat-shrunk in place after the O-ring 212 has been placed in cavity 218. The recess 218 in molded member 216 is sized to receive and retain this O-ring 212 within the left-hand portions of this molded member 216. This shrink-wrap sleeve 210 provides external protection for the filter portions 236. This sleeve does not extend forwardly to the extent the front of the V-grooves 234 become blocked off.

The sharpened end 208 of the injection needle 202 is now advanced forwardly (to the right) whereby the surface 206 of the hub engages the O-ring 212 and expands this O-ring 212 to effect a seal against the recess 218. The ribs 204 pass within and adjacent the fin-like portions 220 formed in member 216. The tapered recess 238 provides a guideway for the injection needle 202 as it enters the bore 226 in the cannula 228 and exits to extend beyond the said cannula. As seen in FIG. 11, the arrows indicate that atmospheric air flows through the V-grooves 234 to and through the filter membrane 236, thence through the air passageway between the injection needle and cannula. The rubber-like properties of the silicone rubber O-ring not only provide a seal, but when withdrawal of the injection needle from the filter assembly is desired this silicone rubber provides non-adhering properties for easy separation while the shrink sleeve 210 prevents rearward movement of said O-ring. The needle shield 232 is removed before the needle with vent filter device is inserted into a resilient stopper.

The several embodiments are depicted in part to illustrate the different molded forms of holding a vent membrane. These showings anticipate the vent's communicating with the annular space between the injecting needle and the sleeve needle. The area of venting capacity of the filter membrane is made to suit the requirements of the apparatus.

The novelty of the several embodiments described above and to be hereinafter claimed is that the injecting needle is of conventional size and that the sleeve needle provides the outer sheath and is assembled so that the fluid path for sterility purposes is not compromised (invaded or broken). This needle assembly is made of a size which enables it to be used with even the smaller vials. The stoppers in such smaller vials usually will accommodate needles of eighteen gauge and smaller. Larger gauge sizes than this cause difficulties and often lead to "coring" and/or leakage, which are undesirable. These cause loss of seal and/or generation of substantial quantities of particulates.

A conventional injecting needle and syringe are anticipated as being employed with outer member as used with this injection needle and providing venting means for withdrawal of any diluent, reconstitution and withdrawal of the now-mixed medication. The injecting needle is unsheathed to provide a ready-for-use condition and the outer vent assembly portions are discarded. The medication in the now ready-for-use filled syringe has not been exposed to unwanted contaminants.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the needle with vent filter assembly may be constructed or used.

While particular embodiments of the needle with vent filter assembly have been shown and described, it is to be understood that the invention is not limited thereto and protection is sought to the broadest extent the prior art allows.

What is claimed is:

1. A needle with a vent filter assembly for use in the aspiration of a drug solution from a supply into a syringe after an outer needle shield is removed so that an injecting needle is exposed and ready for use with an attached syringe containing said drug solution and for the injection of said drug solution into a patient, this vent filter assembly including:

(a) a metal injecting needle of conventional construction and configuration and fixedly attached to a hub portion conventionally formed with a recess adapted to mount on the discharge end of a syringe;

(b) a large barrel shaped tubular vent housing of molded plastic and having an open rear end and front end and a through passageway for the injection needle, the rear end formed with a rear bore extending inwardly from the rear end, with said bore sized and adapted to extend a short distance inwardly from termination of the rear end and adapted to be slideably mounted on the forward end of said needle hub, and in which there are provided and formed a plurality of inwardly-extending ribs which engage and secure a tubular filter membrane in a desired intermediate position within said molded housing, said ribs on their inner extents providing a guideway for the insertion of and withdrawal of the injecting needle, this tubular vent housing having its midportion formed with a plurality of through apertures providing for passage of air from the exterior to the interior and from the interior to the exterior through said secured filter membrane, and configuring these ribs so that at their rearward face each rib terminates in a formed surface to provide a stop abutment surface, these abutment surfaces positioned a short distance inward from the rear termination of the vent housing;

(c) a hydrophobic filter membrane of a tubular configuration having an interior diameter larger than the needle hub and held in position in the midportion of said housing so that all air from and to said supply is caused to pass through said filter;

(d) a rigid cannula portion which is molded with and hub is molded and is an integral part of the vent housing, said cannula sized and positioned so as to provide a forward reduced diameter portion of the housing, this cannula providing a slide guide and surrounding wall member for said injecting needle, said cannula and said injecting needle providing an annular space therebetween sufficient for a pathway along which air can and does flow, said rigid cannula, when said tubular vent housing is in mounted condition, having its entering end terminating before a sharpened end portion of the injecting needle, said sharpened end and rigid cannula sized so as to pierce a stopper and the like of a vial;

(e) a resilient O-ring mountable in said rear bore and sized to engage said bore and the abutting surface of the molded ribs, and in mounted condition to be substantially within said bore, said O-ring providing for hermetically sealing the hub of the injecting needle and the tubular vent housing to prevent an unwanted flow of air while with manipulation being able to separate and withdraw the injecting needle from the rigid cannula;

(f) a plurality of shallow exterior grooves formed in the larger barrel portion of the tubular vent housing, said grooves extending from the formed vent filter apertures to a forward end of said larger barrel portion housing, these shallow grooves providing air flow paths to and from the filter, and (g) a thin, tubular shrink-wrap retainer which is positioned and with heat is affixed to the larger barrel portion of the molded tubular vent housing and with said shrink-wrap open to the front so that said shallow grooves are open to the front of the housing, with said shrink-wrap providing an exterior protective member of and for the outwardly-exposed surface of the filter membrane, and with the rear end of the shrink-wrap extending rearwardly of the tubular vent housing so that when the shrink-wrap film is affixed this extending portion is caused to be turned inwardly and transversely on the outer surface of said tubular vent housing this shrink-wrap portion extending sufficiently inward to provide a retaining means for the mounted O-ring seal, the retained O-ring stopped in its forward travel by the abutment surfaces formed on the inwardly-extending ribs, and in mounted and retained condition said O-ring engages the bore of the housing and the needle hub portion to effect and provide a seal of said passageway so there is provided a protected pathway for air to pass to and from the outside atmosphere to the interior of said tubular vent housing, with said filter removing unwanted contaminants from said air pathway.

2. A needle with vent filter assembly as in claim 1 in which the forward-end portion of the molded tubular housing is provided with a plurality of supporting ribs for the removable mounting thereon of a needle protector, and the shallow exterior grooves formed in said housing are V-shaped.

3. A needle with vent filter assembly as in claim 1 in which the O-ring is of silicone rubber.

4. A needle with vent filter assembly as in claim 3 in which the grooves formed in the molded tubular filter housing have their rearward face portions formed with a slope and the passageway from the ribs to the pathway between the rigid cannula and needle is formed with a taper that provides a guideway for an entering needle.

* * * * *